(12) United States Patent
Sadozai et al.

(10) Patent No.: US 8,124,120 B2
(45) Date of Patent: Feb. 28, 2012

(54) CROSSLINKED HYALURONIC ACID COMPOSITIONS FOR TISSUE AUGMENTATION

(75) Inventors: Khalid K. Sadozai, Shrewsbury, MA (US); Tamera B. Gooding, Jamaica Plain, MA (US); Kyle Bui, North Andover, MA (US); Charles H. Sherwood, Sudbury, MA (US)

(73) Assignee: Anika Therapeutics, Inc., Woburn, MA (US)

( * ) Notice: Subject to any disclaimer, the term of this patent is extended or adjusted under 35 U.S.C. 154(b) by 1639 days.

(21) Appl. No.: 10/743,557

(22) Filed: Dec. 22, 2003

(65) Prior Publication Data

US 2005/0136122 A1 Jun. 23, 2005

(51) Int. Cl.
*A61F 2/08* (2006.01)
*A61F 2/10* (2006.01)
*A61F 2/04* (2006.01)

(52) U.S. Cl. .................................. 424/426; 424/491

(58) Field of Classification Search ................. 424/491, 424/426
See application file for complete search history.

(56) References Cited

U.S. PATENT DOCUMENTS

| | | | |
|---|---|---|---|
| 3,949,073 A | 4/1976 | Daniels et al. | |
| 4,424,208 A | 1/1984 | Wallace et al. | |
| 4,582,640 A | 4/1986 | Smestad et al. | |
| 4,803,075 A | 2/1989 | Wallace et al. | |
| 4,851,521 A | 7/1989 | della Valle et al. | |
| 4,937,270 A | 6/1990 | Hamilton et al. | |
| 4,957,744 A | 9/1990 | della Valle et al. | |
| 5,128,326 A | 7/1992 | Balazs et al. | |
| 5,143,724 A * | 9/1992 | Leshchiner et al. | 424/78.08 |
| 5,246,698 A | 9/1993 | Leshchiner et al. | |
| 5,258,028 A | 11/1993 | Ersek et al. | |
| 5,306,500 A | 4/1994 | Rhee et al. | |
| 5,336,767 A | 8/1994 | della Valle et al. | |
| 5,399,351 A | 3/1995 | Leshchiner et al. | |
| 5,523,291 A | 6/1996 | Janzen et al. | |
| 5,633,001 A | 5/1997 | Ågerup | |
| 5,672,301 A | 9/1997 | Orly et al. | |
| 5,792,478 A | 8/1998 | Lawin et al. | |
| 5,827,937 A | 10/1998 | Ågerup | |
| 5,942,241 A * | 8/1999 | Chasin et al. | 424/426 |
| 6,039,970 A | 3/2000 | Callegaro et al. | |
| 6,066,340 A | 5/2000 | Callegaro et al. | |
| 6,231,613 B1 | 5/2001 | Greff et al. | |
| 6,251,876 B1 | 6/2001 | Bellini et al. | |
| 6,277,392 B1 | 8/2001 | Klein | |
| 6,288,043 B1 | 9/2001 | Spiro et al. | |
| 6,418,934 B1 | 7/2002 | Chin | |
| 6,497,887 B1 | 12/2002 | Zecchino et al. | |
| 6,521,223 B1 * | 2/2003 | Calias et al. | 424/78.08 |
| 6,544,503 B1 | 4/2003 | Vanderhoff et al. | |
| 6,593,308 B2 * | 7/2003 | Szoka, Jr. | 514/54 |
| 6,699,471 B2 * | 3/2004 | Radice et al. | 424/93.7 |
| 7,196,180 B2 * | 3/2007 | Aeschlimann et al. | 536/18.7 |
| 2002/0049281 A1 * | 4/2002 | Zhao et al. | 525/54.3 |
| 2002/0050659 A1 * | 5/2002 | Toreki et al. | 264/4.1 |
| 2002/0071855 A1 | 6/2002 | Sadozai et al. | |
| 2002/0076810 A1 | 6/2002 | Radice et al. | |
| 2003/0060447 A1 | 3/2003 | Karakelle et al. | |

FOREIGN PATENT DOCUMENTS

| | | |
|---|---|---|
| EP | 0 416 250 A2 | 3/1991 |
| EP | 0416250 A2 | 3/1991 |
| EP | 0 341 745 B1 | 12/1994 |
| EP | 0 397 652 B1 | 6/1996 |
| EP | 0 587 106 B1 | 7/1997 |
| EP | 0 265 116 B1 | 3/1998 |
| EP | 0 466 300 B1 | 5/1998 |
| EP | 0 655 945 B1 | 7/1998 |
| EP | 079 446 B1 | 11/1999 |
| EP | 0 839 159 B1 | 8/2001 |
| EP | 0 771 179 B1 | 8/2003 |
| JP | 2000230001 A * | 8/2000 |
| JP | 200239305 | 9/2000 |
| RU | 2128055 | 3/1999 |
| WO | WO 87/07898 | 12/1987 |
| WO | WO 92/20349 | 11/1992 |
| WO | WO-92/20349 A1 | 11/1992 |
| WO | WO-94/02517 | 2/1994 |
| WO | WO 94/02517 | 2/1994 |
| WO | WO 9602209 A1 * | 7/1994 |
| WO | WO 94/21299 | 9/1994 |
| WO | WO 9602209 A1 | 2/1996 |
| WO | WO 97/04012 | 2/1997 |
| WO | WO-02/09792 | 2/2002 |
| WO | WO 02/09792 A1 | 2/2002 |

OTHER PUBLICATIONS

Official Action, Russian Patent Application No. 2006126693, mailed Dec. 26, 2007, (4 pages).
First Office Action, Chinese Patent Application No. 200380111009X, mailed Nov. 23, 2007, (5 pages).
Barbucci, R. et al., "Hyaluronic Acid Hydrogel in the Treatment of Osteoarthritis," *Biomaterials* 23:4503-4513 (2002).
Milas, M., et al., "Comparative Rheological Behavior of Hyaluronan from Bacterial and Animal Sources with Cross-Linked Hyaluronan (Hylan) in Aqueous Solution," *Biopolymers* 59:191-204 (2001).

(Continued)

*Primary Examiner* — Fereydoun G Sajjadi
*Assistant Examiner* — Courtney Brown
(74) *Attorney, Agent, or Firm* — Wilmer, Cutler, Pickering, Hale & Dorr LLP.

(57) ABSTRACT

Disclosed are hyaluronic acid (HA) compositions including crosslinked, water-insoluble, hydrated HA gel particles. Also disclosed are methods of making the HA compositions, and methods of using the HA composition to augment tissue in a subject.

11 Claims, 7 Drawing Sheets

OTHER PUBLICATIONS

Duranti, MD, F., et al., "Injectable Hyaluronic Acid Gel for Soft Tissue Augmentation a Clinical and Histological Study," *The American Society for Dermatologic Surgery, Inc.*, 24:1317-1325 (1998).
Chen, J., et al., "Polysacccharide Hydrogels for Protein Drug Delivery," *Carbohydrate Polymers* 28 (1995) 69-76.
Examiners Report issued for Australian Appl. No. 2009200708, dated May 28, 2010 (5 pages).
Canadian Office Action issued for 2,551,121, issued on Apr. 11, 2011 (3 pages).
Chen, J. et al., "Polysaccharide hydrogels for protein drug delivery," Carbo. Polymers, Appl. Science Publ., Ltd., vol. 28(1): 69-76 (1995).
European Office Action issued for EP03819294.4, dated Apr. 7, 2011 (5 pages).

* cited by examiner

CROSSLINKED HYALURONIC ACID COMPOSITIONS FOR TISSUE AUGMENTATION

BACKGROUND OF THE INVENTION

Currently, all tissue augmentation fillers approved by the United States Food and Drug Administration are derived from collagen. Approximately 3-5% of human subjects show serious allergic reactions to bovine collagen, thus requiring careful testing before using these fillers in any particular subject.

Hyaluronic acid, also referred to as "HA," is a naturally occurring, water soluble polysaccharide that is a major component of the extra-cellular matrix and is widely distributed in animal tissues. Naturally occurring HA generally has a molecular weight range of about between $6 \times 10^4$ to about $8 \times 10^6$ Daltons. It has excellent biocompatibility and does not give a foreign body or allergic reaction when implanted into a subject.

Methods of preparing commercially available hyaluronan are well known. Also known are various methods of coupling HA and cross-linking HA to reduce the water solubility and diffusibility of HA, and to increase the viscosity of HA. See, for example, U.S. Pat. Nos. 5,356,883 and 6,013,679, the entire teachings of which are incorporated herein by reference. Further, many forms of HA have been employed, e.g., as surgical aids to prevent post operative adhesions of tissues, as adjuncts to synovial fluid in joints, as fluid replacement and/or surgical aids in ophthalmic surgery, as a scaffold for tissue engineering in vitro or guided tissue regeneration or augmentation in vivo, and the like.

The use of such HA products suffers several defects, however, in particular, a tradeoff between in vivo properties and surgical usability. For example, HA that is sufficiently chemically modified or crosslinked to have desirable in vivo mechanical and biostability properties can be so highly viscous that injection through fine needles is difficult or impossible. Conversely, HA that is injectable can have inferior in vivo biostability and mechanical properties.

Further, there is high current interest in employing chemically modified HA for vehicle-assisted time release delivery of bioactive agents including, for example, therapeutic agents or drugs and biological probes. A major challenge is the development of a delivery vehicle that will provide the appropriate level of bioavailability of a therapeutic agent at the affected area to achieve a desired clinical result, yet also have a desirable balance of in vivo mechanical and biostability properties balanced with surgical/administrative usability. The bioavailability of a drug depends upon the nature of the drug, the drug delivery vehicle used, and the route of delivery, for example, oral, topical, transdermal, mucosal, administration by injection, administration by inhalation, or administration by a combination of two or more of these routes. The bioavailability may be low as a result of, for example, the degradation of the drug by metabolic processes, rapid or uneven degradation of the delivery vehicle, rapid or uneven release of the drug from the delivery vehicle, and the like. These can be accompanied by similar problems of frequency of administration, difficulty of administration, e.g., difficulty of injection, biodegradation, and the like. In addition to the difficulties noted above, frequent administration of insufficiently stable drug delivery vehicles can lead to variations in drug delivery, leading to an increase in the occurrence of damaging side effects, a decrease in therapeutic benefit, and the like.

Therefore, there is a need for a HA composition that overcomes or minimizes the above referenced problems.

SUMMARY OF THE INVENTION

The invention is directed to a hyaluronic acid (HA) composition and a method of making and using a HA composition that is effective for tissue augmentation and/or drug delivery.

A hyaluronic acid (HA) composition includes crosslinked, water-insoluble, hydrated HA gel particles. The HA includes crosslinks represented by the following structural formula:

Each HA' is the same or different crosslinked HA' molecule, e.g., the crosslinks can be intramolecular or intermolecular.

Each U is independently an optionally substituted O-acyl isourea or N-acyl urea.

R2 is optionally substituted alkyl, alkenyl, alkynyl, alkoxy, cycloalkyl, cycloalkenyl, cycloalkynyl aryl, heteroaryl, heterocyclyl, cycloaliphaticalkyl, aralkyl, heteroaralkyl, or heterocyclylalkyl.

A method of augmenting tissue in a subject that is in need of tissue augmentation includes the step of inserting a needle into a subject at a location in the subject that is in need of tissue augmentation, wherein the needle is coupled to a syringe loaded with the HA composition. Also included is applying force to the syringe, whereby at least a portion of the HA composition is delivered into the subject.

A method of preparing the HA composition, includes forming water-insoluble, dehydrated crosslinked HA particles, separating the water-insoluble, dehydrated particles by average diameter, selecting a subset of particles by average diameter, and hydrating the subset of dehydrated particles with a physiologically compatible aqueous solution, thereby forming the HA composition.

Another method of preparing the crosslinked HA composition includes crosslinking a precursor of the crosslinked HA with a biscarbodiimide in the presence of a pH buffer that is at a pH between about 4 and about 8, and dehydrating the crosslinked HA to produce the dehydrated, crosslinked HA.

A method of stabilizing crosslinked HA includes hydrating water-insoluble, dehydrated crosslinked HA with a physiologically compatible aqueous solution, thereby forming the stabilized HA composition, wherein the physiologically compatible aqueous solution includes at least about 0.1% by weight of a local anesthetic, wherein the value of storage modulus G' for the stabilized composition is at least about 110% of the value of G' measured for a non-stabilized composition, when measured at 37° C. and 1 Hz frequency using a 4 cm flat geometry.

Also included is the stabilized HA composition.

The embodiments disclosed herein are effective for preparing and using crosslinked, water-insoluble, hydrated HA gel particles, wherein the crosslinks in the HA include linking group R2, that have improved combinations of in-vivo biostability and mechanical properties, while at the same time having improved usability, e.g., improved ease of injection through fine needles. For example, as shown in the Exemplification, the HA compositions have improved values for storage modulus G' and kinematic viscosity, while exhibiting improved in vitro and in vivo biostability to hyaluronidase enzyme. The disclosed embodiments are effective for employing crosslinked HA in tissue augmentation while reducing the frequency of implantation needed. The embodiments are also effective for employing crosslinked HA as a drug delivery vehicle that exhibits the surprising and unexpected effect of increasing biostability along with effective drug release properties and effective administrative properties.

DETAILED DESCRIPTION OF THE INVENTION

The invention is directed to crosslinked HA compositions, their preparation, and their methods of use.

Uncrosslinked HA, e.g., the precursor to the crosslinked HA of the invention, typically comprises disaccharide units of D-glucuronic acid (GlcUA) and N-acetyl-D-glucosamine (GlcNAc), which are alternately linked, forming a linear polymer. HA often occurs naturally as the sodium salt, sodium hyaluronate. HA, sodium hyaluronate, and preparations of either HA or sodium hyaluronate are often referred to as "hyaluronan." As used herein, the terms "HA" and "hyaluronan" also refer to any of the other hyaluronate salts, including, for example, potassium hyaluronate, magnesium hyaluronate, calcium hyaluronate, and the like. The uncrosslinked HA used as precursors for the crosslinking typically has an average molecular weight range of from between about $6 \times 10^4$ to about $8 \times 10^6$ Daltons, or 150 to 20,000 disaccharide repeat units. HA from any of a variety of sources, including HA extracted from animal tissues or harvested as a product of bacterial fermentation, can be used as a starting material. Alternatively, the uncrosslinked HA used to make the composites of this invention can be produced in commercial quantities by bioprocess technology, as described, for example, in Nimrod et al., PCT Publication No. WO 86/04355, the entire teachings of which are incorporated herein by reference.

Crosslinked HA can be formed by reacting uncrosslinked HA with a crosslinking agent under suitable reaction conditions. The crosslinked HA is prepared by reacting uncrosslinked HA with a biscarbodiimide in the presence of a pH buffer, wherein the buffer is at a pH between about 4 and about 8. The pH of the buffer can be between about 4 and about 7, typically between 5 and about 6.5, or more typically between about 5 and about 6. In a preferred embodiment, the pH is about 5.5.

The pH buffer can include any buffer agent known to one skilled in the art, e.g., 2-(N-morpholino)ethanesulfonic acid (MES); 2,2-bis(hydroxymethyl)-2,2',2"-nitrotriethanol; succinate/succinic acid; $KH_2PO_4$; N-tris(hydroxymethyl-2-aminoethanesulfonic acid; triethanolamine; diethylbarbituate; tris(hydroxymethyl)aminoethane; N-tris(hydroxy)methylglycine; and N,N-bis(2-hydroxyethyl)glycine. The buffer agent can be employed with an additional acid or base, e.g., 2-(N-morpholino)ethanesulfonic acid with NaOH; 2,2-bis (hydroxymethyl)-2,2',2"-nitrotriethanol with HCl; succinate with succinic acid; $KH_2PO_4$ with borax; N-tris(hydroxymethyl-2-aminoethanesulfonic acid with NaOH; triethanolamine with HCl; diethylbarbituate with HCl; tris(hydroxymethyl)aminoethane with HCl; N-tris(hydroxy)methylglycine with HCl; and N,N-bis(2-hydroxyethyl)glycine with HCl. Preferably, the buffer includes 2-(N-morpholino)ethanesulfonic acid and NaOH.

Typically, the buffer agent is mixed in aqueous media, in a concentration between about 5 mM (millimolar) and about 250 mM, typically between about 10 mM and about 150 mM, more typically between about 25 and about 100 mM, and preferably about 75 mM.

Typically, the uncrosslinked HA is mixed in aqueous media, e.g., the pH buffer solution, in a concentration between about 1 mM (millimolar) and about 100 mM, typically between about 10 mM and about 50 mM, more typically between about 25 and about 50 mM, and preferably about 37 mM. The particular concentration employed can vary depending on the molecular weight of the uncrosslinked HA precursor. At lower concentrations, the reactions can be slower. At higher concentrations, the product can be difficult to handle due to the increase in viscosity. Examples of acceptable concentrations of uncrosslinked HA for other crosslinking reactions are described in U.S. Pat. No. 5,356,883, to Kuo et al., the teachings of which are incorporated herein by reference in their entirety.

The reaction can be carried out at a temperature range of between about 0° C. and about 60° C., typically between about 10° C. and about 40° C., more typically between about 15° C. and about 30° C., and preferably about 25° C. Exemplary reaction conditions can be found in Examples 1-9.

The biscarbodiimide can be combined with the uncrosslinked HA solution alone, or more typically as a solution in a water-miscible organic solvent, e.g., acetone, methyl ethyl ketone, dimethylformamide, dimethyl sulfoxide, methanol, ethanol, 2-propanol, acetonitrile, tetrahydrofuran, N-methyl pyrrolidone, and the like. More typically, the solvent is acetone, and the biscarbodiimide is at a concentration of between about 0.1 mg/mL and about 100 mg/mL, typically between about 1 mg/mL and about 50 mg/mL, more typically between about 5 mg/mL and about 25 mg/mL, and preferably about 15 mg/mL.

The uncrosslinked HA and the biscarbodiimide can be combined in any molar equivalent ratio, e.g., between about 1% and about 200%, typically between about 10% and about 150%, more typically between about 18% and about 125%. In various embodiments, the molar equivalent ratio is about 18%; or about 38%, or about 50%, or about 75%, or about 100%, or about 125%.

A HA composition crosslinked with the biscarbodiimide can include crosslinks characterized by a linking group R2 of the biscarbodiimide agent included in the crosslink, e.g., the linking group connecting through a group U at each end to a HA' molecule, as shown in the following structural formula:

Each HA' in the preceding formula can be different or the same HA' molecule, e.g., the crosslink can be an intermolecular or intramolecular crosslink. Each U can be the same or different and is an optionally substituted N-acyl urea or O-acyl isourea, as shown in the bracketed fragments in the following structural formulas:

[O-acyl isourea]     [N-acyl urea]

These crosslinks can be generated in the reaction of HA' with a biscarbodiimide crosslinking reagent, represented in the following structural formula:

wherein two carbodiimides, substituted with R1, are connected through the linking group R2.

In the preceding structural formulas, each R1 can be the same or different and is an optionally substituted group selected from hydrogen, aliphatic (e.g., alkyl, alkenyl, alkynyl), alkoxy, cycloaliphatic (e.g., cycloalkyl, cycloalkenyl, and cycloalkynyl), aryl, heteroaryl, heterocyclyl, cycloaliphaticalkyl, aralkyl, heteroaralkyl, heterocyclylalkyl, and the like. Suitable optional substituents are those that do not substantially interfere with the properties of the resulting crosslinked HA composition and are described herein in the section describing each of the respective groups. In other embodiments, R1 is an optionally substituted aliphatic group. More preferably, R1 is alkyl, e.g., C1-C6 linear or branched alkyl, e.g., methyl, ethyl, propyl, butyl, 2-propyl, tert-butyl, and the like. Preferably, each R1 is ethyl.

Each R2 is an optionally substituted linking group including one or more of aliphatic, cycloaliphatic, aryl, heteroaryl, heterocyclyl, cycloaliphaticalkyl, aralkyl, heteroaralkyl, heterocyclylalkyl, groups, and the like. Suitable optional substituents are those that do not substantially interfere with the properties of the resulting crosslinked HA composition and are described herein in the section describing each of the respective groups. R2 can optionally include or be interrupted by other groups, e.g, carbonyl, amide, oxy, sulfide, disulfide, and the like. In other embodiments, R2 is a cycloaliphatic, aryl, heteroaryl, or heterocyclyl group. In still other embodiments, R2 is 1,6-hexamethylene octamethylene, decamethylene, dodecamethylene, PEG, —CH$_2$CH$_2$—S—S—CH$_2$CH$_2$—, para-phenylene-S-S-para-phenylene, meta-phenylene-S-S-meta-phenylene, meta-phenylene or para-phenylene. More preferably, R2 is phenylene. Preferably, R2 is para-phenylene.

In one embodiment, the biscarbodiimide is selected from 1,6-hexamethylene bis(ethylcarbodiimide), 1,8-octamethylene bis(ethylcarbodiimide), 1,10 decamethylene bis(ethylcarbodiimide), 1,12 dodecamethylene bis(ethylcarbodiimide), PEG-bis(propyl(ethylcarbodiimide)), 2,2'-dithioethyl bis(ethylcarbodiimde), 1,1'-dithio-p-phenylene bis(ethylcarbodiimide); para-phenylene-bis(ethylcarbodiimide), and 1,1'-dithio-m-phenylene bis(ethylcarbodiimide). In a preferred embodiment, the biscarbodiimide is para-phenylene-bis(ethylcarbodiimide). Methods of preparing biscarbodiimides are described in U.S. Pat. Nos. 6,013,679; 2,946,819; 3,231,610; 3,502,722; 3,644,456; 3,972,933; 4,014,935; 4,066,629; 4,085,140; 4,096,334; 4,137,386, 6,548,081, and 6,620,927 the teachings of which are incorporated herein by reference in their entireties.

The reaction of HA with a biscarbodiimide crosslinking reagent, in the presence of an available proton, is believed to comprise protonation in the first step. The acid anion can then attach to the carbon atom of the cation formed, resulting in the formation of an O-acyl isourea intermediate. The acyl group in the intermediate can migrate from the oxygen atom to a nitrogen atom to produce a N-acyl isourea derivative of the HA. It is believed that the O-to-N migration can be incomplete, resulting in a product reaction mixture that can include both the N-acyl urea and the O-acyl isourea. Thus, a crosslink resulting from reaction of a biscarbodiimide with the crosslinked HA precursor typically can contain two O-acyl isoureas connected through R2, as represented in the following structural formula:

or an O-acyl isourea and an N-acyl urea connected through R2, as represented in the following structural formula:

or two N-acyl ureas connected through R2, as represented in the following structural formula:

The mixed products can be used separately or together to prepare the compositions according to embodiments of the invention.

The crosslinked HA can be precipitated by pouring into a water-miscible organic solvent, e.g., acetone, methyl ethyl ketone, dimethyformamide, dimethyl sulfoxide, methanol, ethanol, 2-propanol, acetonitrile, tetrahydrofuran, N-methyl pyrrolidone, and the like, preferably an alcohol, e.g., ethanol. The precipitate can be collected and dried, e.g., under reduced pressure.

The dried crosslinked HA can be formed into particles by any means well known to one in the art, e.g., abrading, grinding, fracturing, and the like, preferably by grinding in a cryogenic mill. Alternatively, the undried crosslinked HA can be cryoprecipitated to form small particles, which can then be dried, or the undried crosslinked HA can be ground in a cryogenic mill and then the resulting particles can be dried.

As used herein, "water-insoluble" and like terms refers to compositions, e.g., the water-insoluble dehydrated particles, or the water insoluble hydrated particles that are heterogeneous when suspended in a sufficient amount of water at room temperature. In one embodiment, "water-insoluble" means that upon placing the particles of the HA composition in water at neutral pH and 25° C. for at least about 2 weeks, the HA in the particles is essentially undissolved, e.g., essentially no HA from the particles becomes freely dissolved in the water. In other embodiments, "water-insoluble" means that the HA in the particles is essentially undissolved after generally at least about 4 weeks under the preceding conditions, typically at least about 6 weeks, more typically at least about 8 weeks, or preferably at least about 12 weeks. In one embodiment, "water-insoluble" means that the HA in the particles is essentially undissolved after at least about 26 weeks under the preceding conditions. As used herein, "freely dissolved" means solvation of HA molecules in the water separately from the hydrated, water-swelled particles.

Moreover, a cross-linked HA derivative can be a hydrogel. As the term is used herein, a "hydrogel" is a cross-linked macromolecular network that can swell in water or biological fluids, and can retain a significant portion of water within its structure without dissolving. As used herein, the term "swelling" refers to the taking up of a liquid, for example water, by a gel with an increase in volume, typically with the addition of heat and pressure. Hydrogels have a large molecular weight that generally cannot be measured by conventional methods and are composed of a polymer backbone and cross-links.

The crosslinked HA particles can be characterized by particle average diameter distribution. The average diameter can be measured as the average diameter of the hydrated particles and/or the average diameter of the dehydrated particles. Typically, the particle average diameter is selected from the group consisting of a hydrated particle average diameter between about 20 µm (micrometers) and about 1000 µm and a dehydrated particle average diameter between about 10 µm and about 500 µm. In other embodiments, the hydrated particle average diameter is between about 40 µm and about 600 µm and a dehydrated particle average diameter between about 20 µm and about 300 µm, or more preferably, the hydrated particle average diameter is between about 50 µm and about 500 µm and the dehydrated particle average diameter is between about 25 µm and about 250 µm.

In a particular embodiment, the HA in the composition consists essentially of the crosslinked, water-insoluble, hydrated HA gel particles. For example, the HA composition in this embodiment can be considered to be a single hydrated particle phase, e.g., any liquid in the composition is essentially contained in the hydrated particles, e.g., there is essentially no free liquid phase. In other embodiments wherein the HA in the composition consists essentially of the crosslinked, water-insoluble, hydrated HA gel particles, certain forms of HA is excluded from the composition, e.g., typically excluded are HA particles or molecules that have an average diameter smaller than about 1 µm, more typically excluded are HA particles or molecules that have an average diameter smaller than about 10 µm, and preferably excluded are HA particles or molecules that have an average diameter smaller than about 20 µm.

As used herein, a "subset" of particles by average diameter means that a collection of particles are characterized by average diameter, and at least some fraction of particles is rejected, e.g., not included in the subset.

In still other embodiments, the particle average diameters are selected, e.g., by sieving or other methods well known to the art, so that particular average diameter distributions can be chosen to result in particular properties in the final composition, for example, as shown in the Examples. Thus, the dehydrated particles can be sieved to separate by average diameter fractions, e.g., as in Example 16, where five average diameter fractions of particles were collected: 0-25 µm, 25-75 µm, 75-125 µm, 125-180 µm, and 180-250 µm.

The various average diameter fractions of a particular composition can be employed to determine a combination of average diameter fractions in various proportions that will result in particular combined properties. Thus, in one embodiment, the water-insoluble, dehydrated particles can be separated into at least two average diameter fractions and the fractions can be combined in a ratio to adjust the properties of the combination, e.g., in Example 17, two fractions containing 125-250 µm, and 0-125 µm are combined in a 1:1 ratio. The resulting composition has a average diameter distribution that is different from the ground particles before sizing, for example, the average diameter distribution can be a multimodal average diameter distribution, e.g., a bimodal average diameter distribution when two average diameter fractions are selected for the composition. The properties of the multimodal composition are built from the properties of the individual average diameter fractions and their amounts in the composition. In another embodiment, the water-insoluble, dehydrated particles can be separated into at least three average diameter fractions, where at least two average diameter fractions are selected and at least one average diameter fraction is rejected.

The dehydrated particles are typically hydrated in the presence of the physiologically acceptable solution (e.g., a saline solution, or a phosphate buffer as provided in the Examples) under conditions including a temperature of at least about 100° C., a pressure of at least about 120 kPa (kilopascals); and a duration of at least about 15 min. Such conditions can be achieved in an autoclave, for example, and can also serve to sterilize the particles. Other conditions include: temperatures of from about 100° C. to about 150° C., typically from about 110° C. to about 140° C., or preferably from about 120° C. to about 140° C.; pressures from about 120 kPa to about 200 kPa, typically from about 120 kPa to about 160 kPa, or preferably from about 130 kPa to about 140 kPa; and durations from about 15-75 min, more typically from about 20 to about 60 min.

Additional contemplated sterilization/hydration techniques include the following. In one embodiment, product can be contacted with a clean steam supply at a temperature of 118-133° C. (typically about 121° C.) and the corresponding steam pressure at saturation (about 103 kPa to about 186 kPa). Evaporative cooling can occur during vacuum or "natural" cooling, e.g., slow venting of steam pressure. In another embodiment, a product can be sterilized at a temperature of 118-133° C. (typically 121° C.) using a mixture of air and steam, preferably circulated, e.g., by fans. Typical pressures are 69 kPa to about 103 kPa over the saturation pressure of the steam (typically less than 310 kPa). Cooling can be achieved, e.g., by the addition of cool air and circulation with the fans. In another embodiment, products can be sprayed with liquid water at the sterilization temperature under sufficient counter pressure to keep the water in the liquid phase (typically less than 310 kPa). Cooling to approximately 80° C. can be achieved by direct contact water spray in heat exchange with a cooling system. Cooling from about 80° C. down to about 20° C. is generally evaporative and can also serve to remove excess liquid from the product. Many variations on the preceding hydration/sterilization techniques are possible.

The crosslinked HA composition preferably includes a physiologically effective amount of at least one bioactive agent selected from the group consisting of cells, genes, proteins, antibodies, peptides, and pharmaceuticals.

A pharmaceutical, as that term is used herein, includes, for example: compounds and compositions recognized in the official United States Pharmacopoeia, the official Homeopathic Pharmacopoeia of the United States, or the official National Formulary, or any supplement thereof; compounds and compositions intended for use in the diagnosis, cure, mitigation, treatment, or prevention of disease in man or other animals; and compounds and compositions (other than food) intended to affect the structure or any function of the body of man or other animals. Pharmaceuticals include pharmaceutical compounds and solvates, salts, crystal polymorphs, and stereoisomers thereof. Examples of classes of pharmaceuticals include growth factors (e.g., interleukins, prostaglandins, thromboxanes, leukotrienes and cytokines), steroidal and non-steroidal contraceptive agents, antibiotics (e.g., penicillin, streptomycin and linocomycin), analgesics, anesthetics, sedatives, barbiturates, aminoalkybenzenes, catecholamines, narcotics, narcotic antagonists, anti-neoplastic agents and anticoagulants (e.g., heparin and heparin sulfate)steroidal and non-steroidal anti-inflammatory drugs, anesthetics, antibiotics, antifungals, hormones and any synthetic analogues and pharmaceutically-active fragments thereof, and the like. Pharmaceuticals which are suitable for use in delivery systems in embodiments of the invention may be fat soluble, water-soluble, anionic or cationic, as long as they can interact with a group on the hyaluronic aid derivative of an embodiment to form either covalent or ionic bonds or hydrophobic or hydrophilic interactions, for example, a hydrophobic interaction between a pharmaceutical having a hydrophobic moiety and the HA derivative according to an embodiment can occur.

The bioactive agent can be introduced at any stage, but is typically added during preparation of the composition by inclusion in the physiologically compatible solution used to hydrate the dehydrated particles, e.g., the phosphate buffer in the Examples. In one embodiment, the crosslinked HA composition, e.g., the hydrated HA particles, includes an anesthetic, e.g., a local anesthetic, as the bioactive agent. A local anesthetic can include at least one member of the group selected from ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. Typically, the bioactive agent is a local anesthetic selected from lidocaine, mepivacaine, prilocaine, bupivacaine, cocaine, procaine, chlorocaine, and tetracaine, or a salt or solvate thereof thereof. Preferably, the bioactive agent is the local anesthetic lidocaine, or a solvate or salt thereof, e.g., the salt lidocaine-HCl.

The crosslinked HA can function as a vehicle which provides the controlled or sustained release of the bioactive agent. In one embodiment, the controlled-release HA is placed in contact with a pre-selected tissue, and allowed to remain in place until a desired clinical result is achieved. The controlled-release HA according to an embodiment may be injected or implanted at the locus where delivery is desired, or may be administered orally or by a route that is a combination of two or more of these administration routes.

Diffusion provides the delivery of a bioactive agent via delivery systems in which the drug non-covalently interacts with the crosslinked HA. Such non-covalent interactions include ionic, hydrophobic, and hydrophilic interactions in which the bioactive agent is dispersed within the carrier. As used herein, the term "dispersed" means ionic, hydrophobic, and hydrophilic interactions between the drug and the HA.

The rate of delivery of a bioactive agent is related not only to the rate of its diffusion, but also to the rate of degradation of the HA in which the drug or other bioactive agent is dispersed. The rate of degradation of the HA is related to the degree of cross-linking and is also dependent on numerous metabolic processes taking place in vivo. The degradation process is usually slower than diffusion. By choosing the concentration of the drug dispersed within the HA, and the degree of cross-linking, the rate of degradation and diffusion and, thus, the rate of drug delivery, can be controlled.

As used herein, a "physiologically effective amount" is the amount of bioactive agent that is sufficient to have the intended effect, e.g., an amount of local anesthetic sufficient to have an anesthetic effect in a subject injected with a composition including the agent. One skilled in the art will be able to determine a physiologically effective amount based on the amount of composition employed, the subject's medical history, and the like. The drug concentration can be varied over very broad limits and preferably should be chosen depending on the degree of cross-linking of the HA, the solubility of the drug, its pharmaceutical activity, and the effect desired.

As used herein, a "physiologically acceptable solution" is any solution known in the art that is useful as a carrier in a physiological system, e.g., aqueous solutions that are typically sterile, non-allergenic, non-toxic, and the like, e.g., a saline solution, a buffer solution, a sugar solution, and the like.

The viscolastic properties of the composition can be determined as shown in the Examples. In one embodiment, the composition has at least one parameter measured at 37° C. selected from a storage modulus G' of at least about 50 Pa (Pascals) when measured at 1 Hz (Hertz) frequency using a 4 cm (centimeter) flat geometry; and a kinematic viscosity of at least about 20,000 cPs (centiPoise) when measured at a shear rate of $1\ s^{-1}$.

In other embodiments, kinematic viscosity is at least about 40,000 cPs, more typically at least about 60,000 cPs, and preferably at least about 70,000 cPs. In another embodiment, the kinematic viscosity is from about 20,000 cPs to about 250,000 cPs. In other embodiments, the kinematic viscosity is from about 40,000 cPs to about 220,000 cPs, more typically from about 60,000 cPs to about 200,000 cPs, and preferably from about 70,000 cPs to about 170,000 cPs.

In other embodiments, the storage modulus G' is at least about 100 Pa, typically at least about 100 Pa, more typically at least about 200 Pa, and preferably at least about 400 Pa. In other embodiments, the storage modulus G' is from about 50 Pa to about 1,600 Pa, typically from about 100 Pa to about 1,200 Pa, more typically from about 200 Pa to about 1000 Pa, and preferably from about 400 Pa to about 700 Pa.

The crosslinked HA composition can be characterized by its biostability, e.g., its resistance to degradation in vitro by hyaluronidase enzyme as shown in the Examples. For example, upon combining the composition at 37° C. with hyaluronidase enzyme in an amount of about 0.3% by weight, under conditions suitable for reaction with hyaluronidase, the value of G' for the composition measured after about 16 hours of reaction is at least about 5% of the value of G' measured at about 15 min of reaction. In other embodiments, the value of G' for the composition measured after about 16 hours of reaction is a fraction of the value of G' measured at about 15 min of reaction of generally at least about 10%, or at least about 25%, or at least about 45%, or at least about 50%, typically at least about 60%; more typically at least about 75%; or preferably, at least about 80%. In one embodiment, the value of G' for the composition measured after about 16 hours of reaction is about the same as the value of G' measured at about 15 min of reaction.

In other embodiments, the storage modulus G' is increased, e.g., the composition is stabilized, by the inclusion of a local anesthetic, e.g., lidocaine, compared to a non-stabilized composition, e.g. an identical composition except that the local anesthetic is not included. For these embodiments, the stabilized and non-stabilized compositions can be compared by measuring the value of G' under the same conditions. A stabilized composition prepared by hydrating dehydrated particles under the hydration conditions disclosed herein with a solution having 0.1% of a local anesthetic (e.g., lidocaine) by weight has a G' greater than G' for a non-stabilized composition of generally at least about 110%, typically at least about 120%, more typically at least about 150%, and preferably at least about 175%.

In a particular embodiment, the HA composition, includes crosslinked, water-insoluble, hydrated HA gel particles. The particles include lidocaine.HCl. Also, the particles have an average diameter selected from the group consisting of a hydrated particle average diameter between about 20 and about 1000 μm, and a dehydrated particle average diameter between about 10 and about 500 μm. Further, the particles include crosslinks represented by the following structural formula:

wherein the variables have the values described above. The composition has at least one parameter measured at 37° C. selected from a storage modulus G' of at least about 50 Pa when measured at 1 Hz frequency using a 4 cm flat geometry, and a kinematic viscosity of at least about 20,000 cPs when measured at a shear rate of $1\ s^{-1}$. Also, the composition is sufficiently stable to enzymatic degradation that upon combining the composition at 37° C. with hyaluronidase enzyme in an amount of about 0.3% by weight, under conditions suitable for reaction with hyaluronidase, the value of G' for the composition measured after 16 hours of reaction is at least about 5% of the value of G' measured at less than about 15 min of reaction. In another embodiment, the value of G' for the composition measured after 16 hours of reaction is at least about 50% of the value of G' measured at less than about 15 min of reaction.

As used herein, "in need of tissue augmentation" means that a subject has a medical condition that can benefit from application of the HA composition of the invention, e.g., the subject is in need of treatment and/or correction of conditions, e.g., wrinkles, furrows and folds and other wrinkles in the skin, typically in the forehead and around the eyes, nose and lips, correction and reforming of soft tissue defects and depressed scars. These conditions can be hereditary or acquired through age, illness, injury, surgical complications, and the like.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Most preferably, the subject is human.

As used herein, alkyl groups include, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl, eicosyl, heneicosyl, docosyl, tricosyl, tetracosyl, pentacosyl and the isomeric forms thereof. An alkoxy group is an alkyl group connected through an oxygen atom, e.g., methoxy, ethoxy, propoxy, and the like.

As used herein, alkenyl groups are alkyl groups of 2 to 25 carbon atoms that contain a double bond, such as vinyl, allyl, butenyl, pentenyl, hexenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and isomeric forms thereof.

As used herein, alkynyl groups are alkyl groups of 2 to 25 carbon atoms that contain a triple bond, such as vinyl, allyl, butynyl, pentynyl, hexynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, and isomeric forms thereof.

The term "aryl" as used herein refers to phenyl, tolyl, xylyl, naphthyl, biphenylyl, triphenylyl, and the like. The term "heteroaryl" refers to heteroaromatic groups, e.g. pyrrolyl, thienyl, furanyl, pyridinyl, oxazolyl, isooxazolyl, thiazolyl, isothiazolyl, quinolinyl, and the like. An aralkyl group is an aryl group connected through an alkyl group, e.g., benzyl, ethylnapthyl, and the like.

As used herein, cycloalkyl includes saturated rings of 3 to 8 carbon atoms, inclusive, such as cyclopropyl, cyclobutyl, cyclopentyl, cyclohexyl, cycloheptyl, cyclooctyl and the like. A cycloalkylalkyl group is a cycloalkyl group connected through an alkyl group, e.g., methylcyclopropyl, and the like.

The term heterocyclyl refers to a cycloalkyl group wherein one or more ring carbon atoms are replaced with a heteroatom, e.g., aziridyl, azetidyl, pyrrolidyl, piperidyl, thiiranyl, thietanyl, tetrahydrothiophenyl, tetrahydrothiopyranyl, oxiranyl, oxetanyl, tetrahydrofuranyl, tetrahydropyranyl, morpholinyl, and the like.

The term "cycloalkenyl" refers to cycloalkyl groups having a double bond, e.g., cyclopropenyl, cyclobutenyl, cyclopentenyl, cyclohexenyl, cycloheptenyl, cyclooctenyl and the like.

The term "cycloalkynyl" refers to cycloalkyl groups having a triple bond, e.g., cyclopropynyl, cyclobutynyl, cyclopentynyl, cyclohexynyl, cycloheptynyl, cyclooctynyl and the like.

The term "substituted" as used herein means a group wherein one or more hydrogen atoms have been replaced with a chemical group which does not adversely affect the desired preparation of the product derivative. Representative of such groups are halogen (e.g., —F, —Cl, —Br, —I), amino, nitro, cyano, —OH, alkoxy, alkyl, aryl, amido, sulfamido, sulfate, sulfonate, phosphate, phosphonate, carboxylate, carboxamido, and the like.

EXAMPLES

Crosslinked HA is prepared in the following examples by reacting a biscarbodiimide with uncrosslinked hyaluronic acid in the described ratios. The molecular weight of the uncrosslinked HA used in these examples was approximately from about $5 \times 10^5$ Daltons to about $2 \times 10^6$ Daltons, though higher or lower molecular weight HA can also be used. The hyaluronic acid used was obtained from rooster combs or bacterial sources. All compounds were obtained from Sigma, St. Louis, Mo., unless otherwise specified.

Preparation of MES-Buffers (pH range 5.2-7.1)

For each MES buffer, 2-[N-Morpholino]ethanesulfonic acid (MES hydrate) (14.6 g) was dissolved in 980 mL of sterile water. For each of three solutions, the pH was adjusted to the desired value (5.5, 6.0, or 6.5) by the addition of 0.1N NaOH. Sterile water was added to bring the volume to 1 L.

Phosphate Buffers 1-5

For each individual phosphate buffer, 1 L of sterile water was used to dissolve the amounts indicated in Table 1 of sodium phosphate dodecahydrate ($Na_3PO_4 \cdot 12H_2O$), lidocaine hydrochloride (Lidocaine·HCl), sodium hydrogen phosphate ($Na_2HPO_4$), and sodium dihydrogen phosphate monohydrate ($NaH_2PO_4 \cdot H_2O$).

TABLE 1

Details phosphate buffers 1-5

| Phosphate buffer # | $Na_3PO_4 \cdot 12H_2O$ | Lidocaine.HCl | $Na_2HPO_4$ | $NaH_2PO_4 \cdot H_2O$ |
|---|---|---|---|---|
| 1 | 3.4 g, 9.0 mM | — | — | — |
| 2 | 3.4 g, 9.0 mM | 2.0 g -> 0.20% | — | — |
| 3 | 3.4 g, 9.0 mM | 3.0 g -> 0.30% | — | — |
| 4 | 2.48 g, 6.50 mM | 3.0 g -> 0.30% | 0.36 g, 2.5 mM | — |
| 5 | — | 3.0 g -> 0.30% | 1.42 g, 10.0 mM | 0.27 g, 2.0 mM |

Procedure for Examples 1-9

In each of the following examples, reagents were used in the amounts indicated in Table 2. Uncrosslinked HA was dissolved in 133.4 mL of MES buffer at the specified pH and combined with a 15 mg/mL acetone solution of p-phenylene-bis(ethylcarbodiimide) (PBCDI), resulting in the specified molar equivalent ratio (MER%) and mol % between PBCDI: HA. The reaction mixture was thoroughly mixed (mixing with either a glass rod or an overhead mechanical stirrer, e.g., for~1 minute, results in a white paste from the clear reaction mixture), and the mixture was allowed to stand at room temperature for about 72 hours. Sodium chloride (6.5 g, to make the mixture 5% by weight of sodium chloride) was mixed into the resulting gel, which was allowed to stand for 1 hour. The crosslinked HA gel was precipitated by addition into about 1.2 L of vigorously stirred ethanol. The precipitate was collected and dried under reduced pressure yielding the crosslinked hyaluronic acid.

TABLE 2

Details for synthesizing crosslinked HA in Examples 1-9.

| Example | PBCDI | | | Acetone | HA | | | | |
|---|---|---|---|---|---|---|---|---|---|
| | mg | mmol | mequiv | mL | g | mmol | MER | mol % | pH |
| 1 | 100 | 0.47 | 0.94 | 6.7 | 2 | 4.98 | 18.7 | 9.4 | 5.5 |
| 2 | 200 | 0.94 | 1.87 | 13.3 | 2 | 4.98 | 37.5 | 18.8 | 5.5 |
| 3 | 267 | 1.25 | 2.5 | 12.6 | 2 | 4.98 | 50 | 25.0 | 5.5 |
| 4 | 400 | 1.87 | 3.74 | 26.7 | 2 | 4.98 | 75 | 37.5 | 5 |
| 5 | 400 | 1.87 | 3.74 | 26.7 | 2 | 4.98 | 75 | 37.5 | 5.5 |
| 6 | 400 | 1.87 | 3.74 | 26.7 | 2 | 4.98 | 75 | 37.5 | 6 |
| 7 | 400 | 1.87 | 3.74 | 26.7 | 2 | 4.98 | 75 | 37.5 | 6.5 |
| 8 | 534 | 2.5 | 5 | 35.6 | 2 | 4.98 | 100 | 50.0 | 5.5 |
| 9 | 667 | 3.12 | 6.2 | 44.5 | 2 | 4.98 | 125 | 62.5 | 5.5 |

Example 10

Degree of Crosslinking Increases with Increasing Molar Ratio of the Crosslinker

Crosslinking of hyaluronic acid with p-phenylene-bis(ethylcarbodiimide) incorporates the phenylene UV chromophore into the crosslinked product. By measuring the UV absorbance of the crosslinked product, the amount of the UV chromophore and degree of crosslinks incorporating the bis-carbodiimide-derived linker can be quantified.

Figure 1:
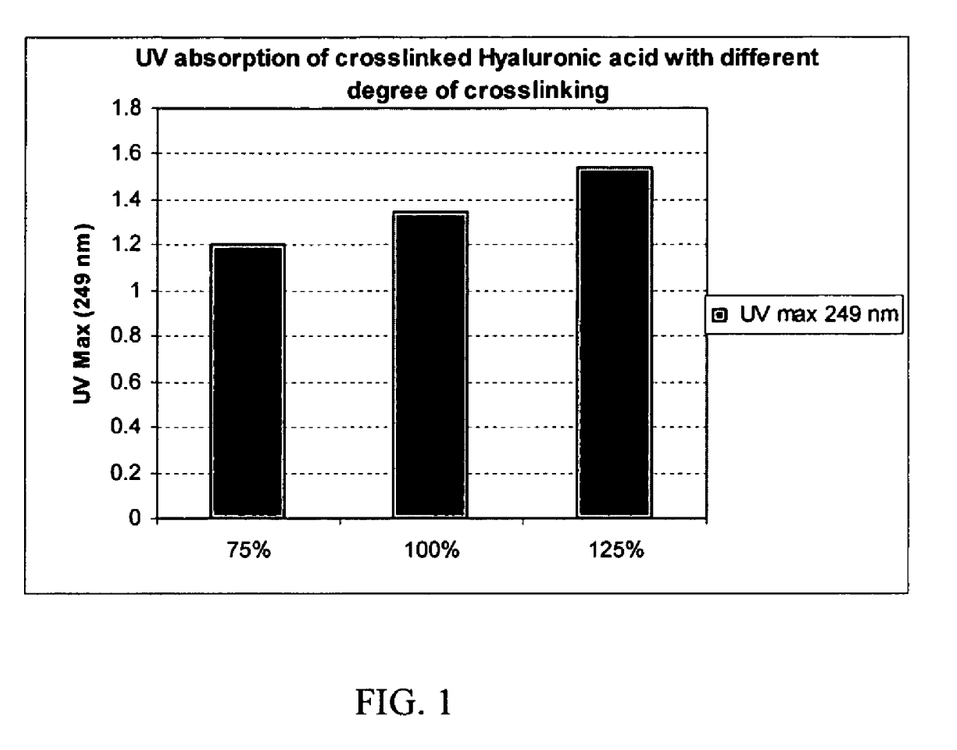
FIG. 1: UV absorbance of the crosslinked products obtained by reacting HA and p-phenylene-bis(ethylcarbodiimide) in a molar equivalent ratio of 75%, 100%, and 125%.

To make a 0.1-mg/mL solution, a weighed amount (1-10 mg) of each of the crosslinked products of Examples 5, 8 and 9 was separately dissolved in a sufficient amount of 5% sulfuric acid solution by heating at 70-75° C. for 4 h in a sealed container. Each solution was diluted with 5% sulfuric acid to make a 0.1-mg/mL solution of each product. The UV absorbance (UV Max) of these solutions measured at 249 nm is shown in FIG. 1 as a function of the biscarbodiimide:HA molar equivalent ratio in %. Thus, a correlation can be seen between the degree of crosslinking incorporating the biscarbodiimide-derived linker (evidenced by UV Max) and the biscarbodiimide:HA molar equivalent ratio in %.

Example 11

Degree of Crosslinking can be Controlled by pH

Figure 2:
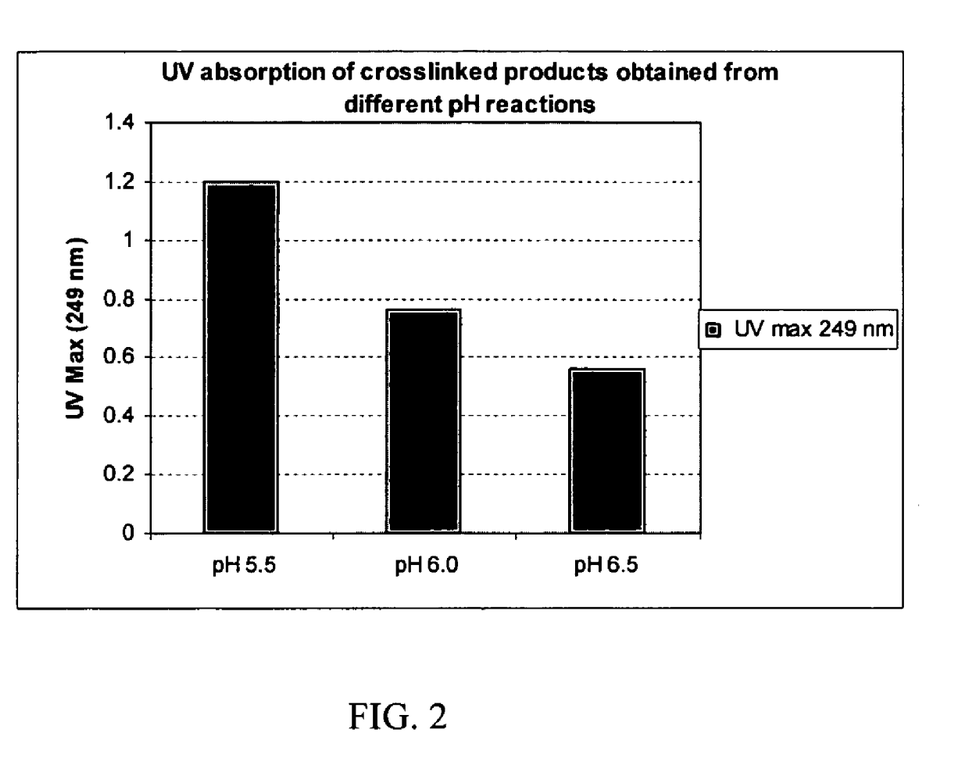
FIG. 2: UV absorbance of the crosslinked products obtained by reacting HA and p-phenylene-bis(ethylcarbodiimide) in MES buffer of pH 5.5, 6.0, and 6.5.

To make a 0.1-mg/mL solution, a weighed amount (1-10 mg) of each of the crosslinked products of Examples 5, 6 and 7 was separately dissolved in a sufficient amount of 5% sulfuric acid solution by heating at 70-75° C. for 4 hour in a sealed container and then allowing to stand for 16 hours at room temperature. These solutions were each diluted with 5% sulfuric acid to make a 0.1-mg/mL solution of each product. The UV absorbance of these solutions measured at 249 nm is shown in FIG. 2.

It can be seen that the degree of crosslinking incorporating the biscarbodiimide-derived linker is greatest at pH 5.5 (the composition of Example 5), which is greater than that at pH 6.0 (the composition of Example 6), which are both greater than that at pH 6.5 (the composition of Example 7).

Example 12

Preparation of a Gel From Dehydrated Crosslinked HA

A portion of the dry crosslinked HA precipitate of Example 5 was milled in a cryogenic mill. The powder was suspended in dimethyl sulfoxide (DMSO) and the suspension was stirred for 4-10 hours. The suspension was centrifuged and the DMSO was removed. The water-insoluble crosslinked HA was re-suspended in ethanol, stirred for a few hours, and the ethanol was removed (the ethanol washing can be repeated if desired). After removing the ethanol, the solid was collected and dried under vacuum. The dried powder of the crosslinked HA was suspended in Phosphate Buffer 4 to make a 30-mg/mL suspension in the form of a slurry or paste. The osmolarity of the suspension was adjusted to 280-340 mOsm (milliosmol) by adding NaCl and loaded into a syringe. The syringe was autoclaved at 120° C. at a pressure of about 138 kPa (kilopascal) (20-lb/in$^2$) for 25 minutes and cooled after sterilization with chilled water.

Example 13

Characterization of Storage Modulus G' of Hydrated HA Gels

The rheological behavior (including storage modulus G') of the gel in Example 12 was evaluated with a Rheometer AR-1000 (TA Instruments, New Castle, Del.). The measuring conditions included a temperature=37° C., a measuring geometry=flat plate, a gap of 200 μm (micrometers), and a frequency of 1 Hz. Under these conditions, the storage modulus G' of the gel prepared in Example 12 was measured to be 1076 Pa (Pascals).

Example 14

Characterization of Extrusion Force of Hydrated HA Gels

The force required to extrude a gel can be characterized by loading the gel in a 1 mL glass syringe [having an internal diameter of 0.635 cm, equipped with a 30-gauge (~150 μm internal diameter, cross-sectional area of 0.0177 mm$^2$) needle. The force required to extrude the gel through the needle at a rate of 4 mL/h was measured by placing the syringe on a syringe pump mounted with a force sensor system (Load Cell SLB-50, Transducer Techniques, Temecula, Calif.). At about 25° C., and an extrusion rate of 4 mL/h, the extrusion force measured was 10.7 N (Newtons) (2.4 pounds).

Example 15

Characterization of Stability of Hydrated HA Gels to Enzymatic Hydrolysis

Durability of the crosslinked hyaluronic acid against enzymatic hydrolysis can be measured by an in vitro test by combining the gel with a measured amount of hyaluronidase enzyme, and recording the storage modulus as a function of time.

To the gel of Example 12 (0.75 g) taken in a vial, was added a solution of hyaluronidase enzyme from bovine testes (15 μL of 0.15 mg/mL solution of hyaluronidase in 1.9 mM phosphate buffer in saline, ~2.5 units) and both were mixed thoroughly for 1 minute. The mixture was filled into a syringe and centrifuged for 1 minute at 1500 rpm to remove air bubbles. 0.35 g of this mixture was loaded on the rheometer plate. Data accumulation was begun at 15 min after addition of the enzyme. The storage modulus G' of the gel was recorded at 10 min intervals for 16 hours at a temperature=37° C., a flat plate measuring geometry, a gap of 200 μm, and a frequency of 1 Hz.

The rate of decrease in storage modulus ΔG'/Δt, e.g., the slope of G' versus time, can be calculated by dividing the value of ΔG' by the time interval,. This rate can represent the susceptibility of the product to enzymatic hydrolysis. In comparing the stability of two compositions, the composition with greater stability maintains G' better than a composition with lesser stability. In this example, the average rate of loss of G' for the gel was about −5 Pa/hour. Thus, the composition in this example can be considered to be stable under the conditions of the test. One skilled in the art can appreciate that a composition that is stable under these conditions can be expected to have good in vivo stability as well.

Example 16

Effect of Particle Size on the Rheological Properties of the Gel

The dry, precipitated crosslinked HA from Example-5 was milled in a cryogenic mill and washed with DMSO and ethanol as described in Example 12. After removing the ethanol, the solid was collected and dried under vacuum. The dried powder of the crosslinked HA was fractionated by average diameter according to five sieves: 25 μm, 75 μm, 125 μm, 180 μm, and 250 μm placed on the top of each other. Five average diameter fractions of particles were collected: 0-25 μm, 25-75 μm, 75-125 μm, 125-180 μm, and 180-250 μm. Each fraction was suspended in Phosphate Buffer 5 to make 32 mg/mL suspension. The osmolarity of the suspension was adjusted to 280-340 mOsm (miliosmol) and each suspension was loaded into a syringe. The syringes were autoclaved at 120° C. at a pressure of about 138 kPa (kilopascal) (20-lb/in$^2$) for about 45 minutes and subsequently cooled with chilled water.

Figure 3:
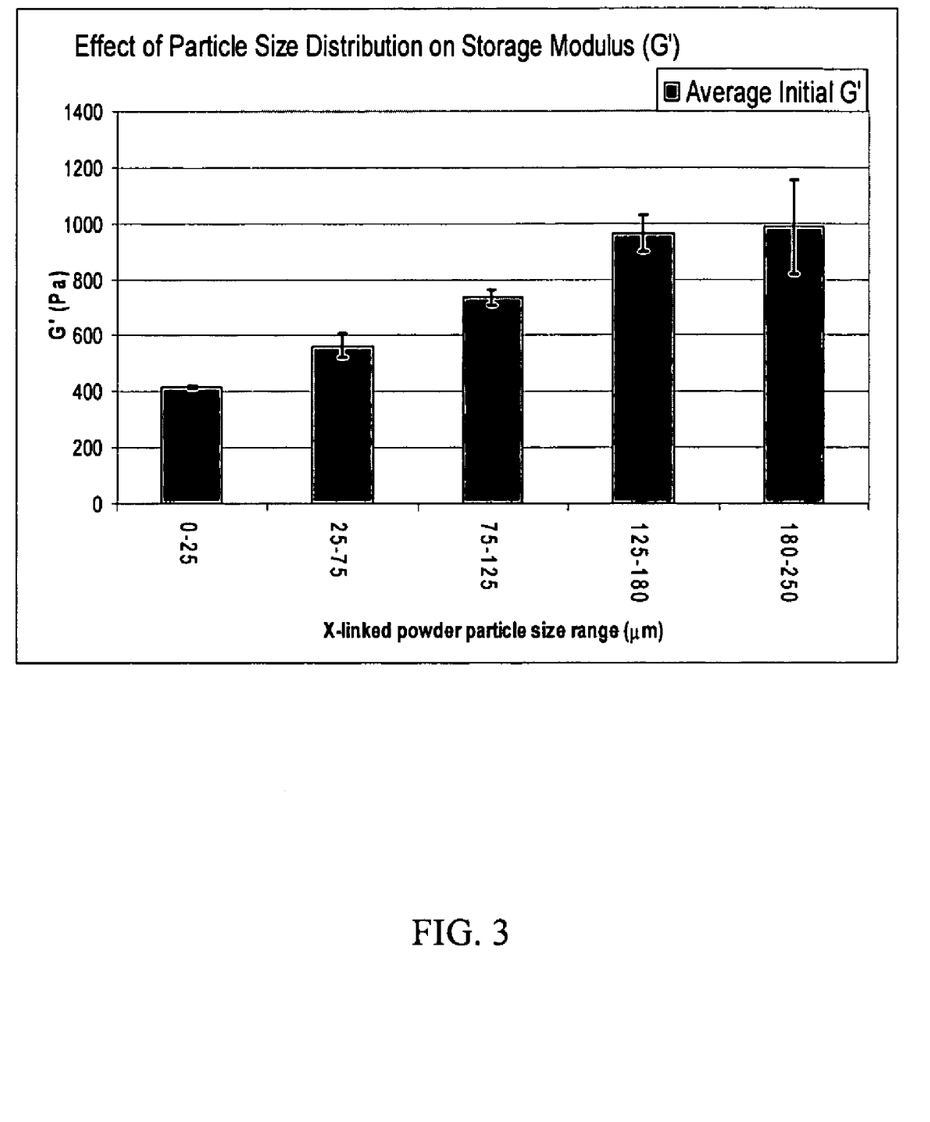
FIG. 3: Effect of the particle average diameter distribution on the storage modulus (G') of the gel.

FIG. 3 shows the storage modulus (G') for each gel, measured under the conditions described in Example-12. As can be seen from the FIG. 3, the rheological properties of these viscoelastic gels were dependent on the particle average diameter distribution and composition of the gels.

Figure 4:
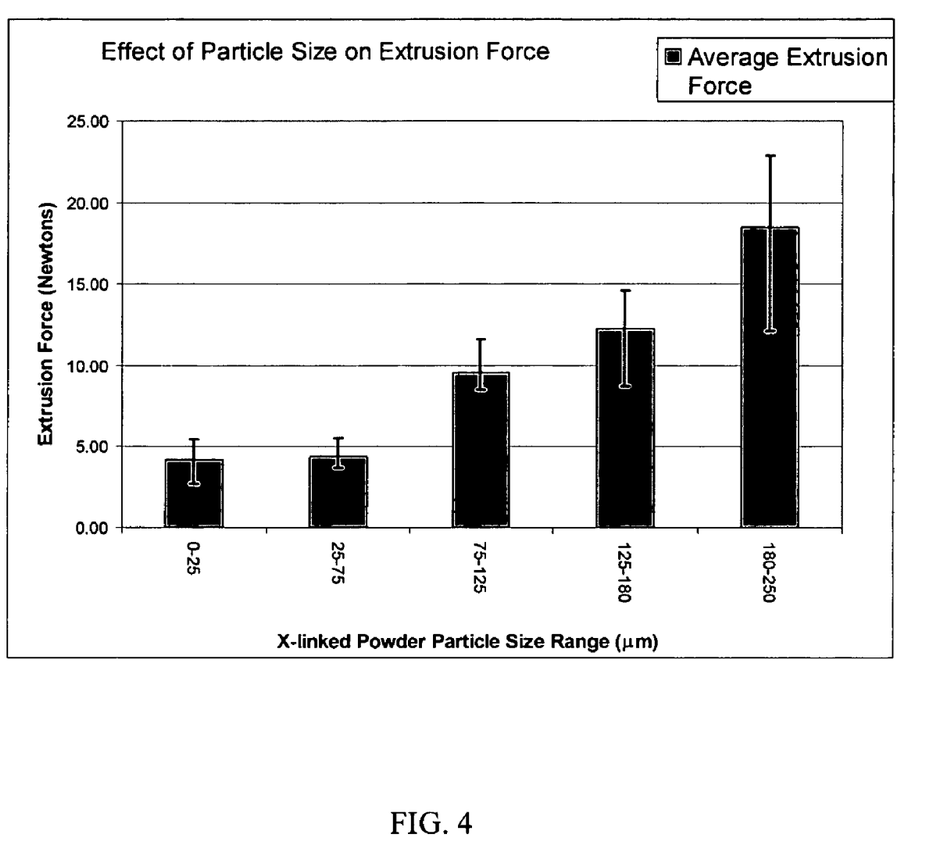
FIG. 4: Effect of the particle average diameter distribution in the gel on the force required to extrude the gel from a 30-gauge needle.

FIG. 4 shows the force required to extrude these gels through a 30 gauge needle according to the procedure described in Example 12. As can be seen in FIG. 4, the extrusion force of these viscoelastic gels was dependent on the particle average diameter distribution and composition of the gels.

Example 17

Combining Particle Size Fractions to Achieve Particular Rheological Properties The dry, precipitated, crosslinked HA from Example 5 was milled and washed as described in Example-12. A portion of the dried powder of the crosslinked HA was then sieved through a 250 μm sieve. All particles of less than 250 μm average diameter were collected and suspended in Phosphate Buffer 4 to make 32-mg/mL suspension.

Two portions having particle average diameters 250-125 μm and less then 125 μm were collected. These fractions were combined in 1:1 ratio by weight and suspended in Phosphate Buffer 4 to make 32-mg/mL suspension. The osmolarity of each suspension was adjusted to 280-340 mOsm (miliosmol) and loaded into a syringe. The syringes were autoclaved at 120° C. at a pressure of about 138 kPa (kilopascal) (20-lb/in$^2$) for about 45 minutes and subsequently cooled with chilled water.

The storage modulus (G') for these gels was measured using the measuring conditions described in Example-12. The gel sample prepared from particles average diameters less than 250 μm had an initial G' of 600 Pa; the gel sample prepared from a 1:1 ratio of 250-125 μm and 125-0 μm particle average diameters had an initial G' of 450 Pa.

Example 18

Storage Modulus Versus Degree of Crosslinking

A portion of the dry, precipitated, crosslinked HA from each of Examples 5 and 6 was milled and washed as described in Example 12. Each portion was sieved through a 250 μm sieve. Particles of less than about 250 µm average diameter were collected and suspended in Phosphate Buffer 4 to make a 32-mg/mL suspension.

The osmolarity of each suspension was adjusted to 280-340 mOsm (miliosmol) and loaded into a syringe. The syringes were autoclaved at 120° C. at a pressure of about 138 kPa (kilopascal) (20-lb/in$^2$) for about 20 minutes and subsequently cooled with chilled water.

The storage modulus (G') for these gels was measured using the measuring conditions described in Example 12. The gel sample prepared from the composition of Example 5 had an initial G' of 700 Pa; the gel sample prepared from the crosslinked composition of Example 6 had an initial G' of 450 Pa. It can be seen that the composition having a higher degree of crosslinking according to the UV crosslinking measurements, the composition of Example 5, also shows a higher storage modulus.

Example 19

ΔG'/Δt for Invention is Superior to Competitive Products

Figure 5:
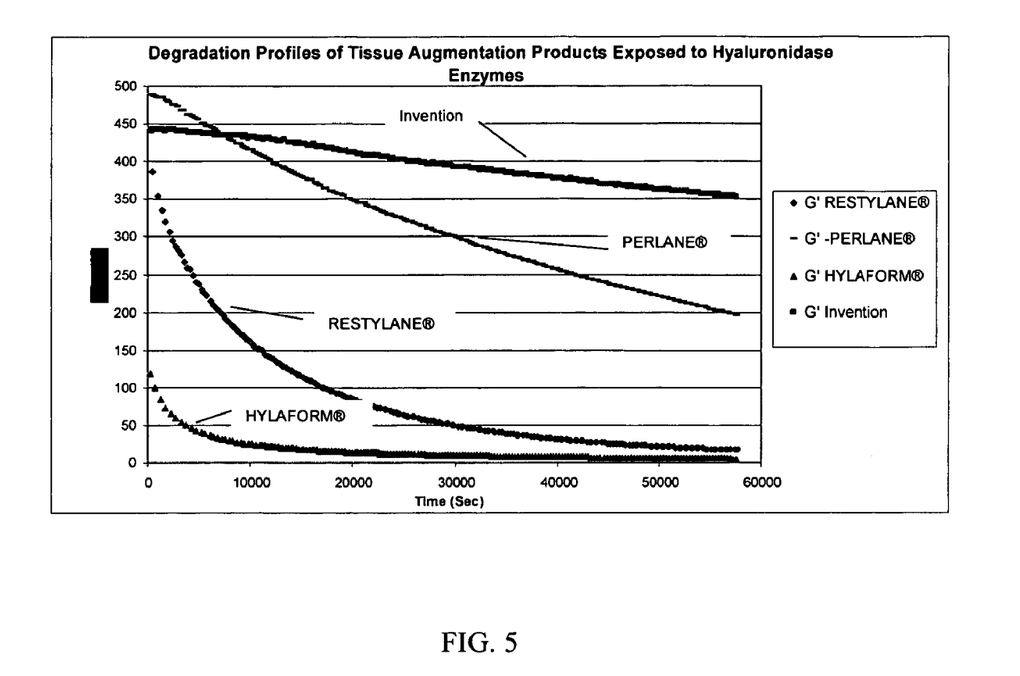
FIG. 5: Degradation of crosslinked HA product in the presence of enzyme hyaluronidase, compared to the other tissue augmentation products RESTYLANE®, PERLANE® and HYLAFORM®

Crosslinked HA obtained according Example 5 and processed according to Example 12 was made into a gel having a initial G' of 450 Pa. The resistance of this product and three competitive tissue augmentation products RESTYLANE®, PERLANE® (both Q-Med, Uppsala, Sweden), and HYLAFORM® (Genzyme, Cambridge, Mass.) to digestion with the hyaluronidase was evaluated. Hyaluronidase solution (15 µL of 0.15 mg/mL solution of hyaluronidase in 1.9 mM phosphate buffer in saline, ~2.5 units) was added and thoroughly mixed with 0.75 g of each product. Each mixture was loaded into a syringe and centrifuged for 1 minute at 1500 rpm to remove air bubbles. 0.35 g of each mixture was then loaded on a rheometer plate. Data accumulation began 15 minutes from the time of addition of the enzyme. The storage modulus G' of the gel was recorded at 10 min intervals for 16 hours at a temperature=37° C., a flat plate measuring geometry, a gap of 200 µm, and a frequency of 1 Hz. FIG. 5 shows G' for each product versus time. As can be see, the rate of loss representing the susceptibility of the product to enzymatic hydrolysis for the invention is much less than that of the three competing compositions.

Example 20

ΔG'/Δt of Compositions Versus Hyaluronidase is Independent of G'

Figure 6:
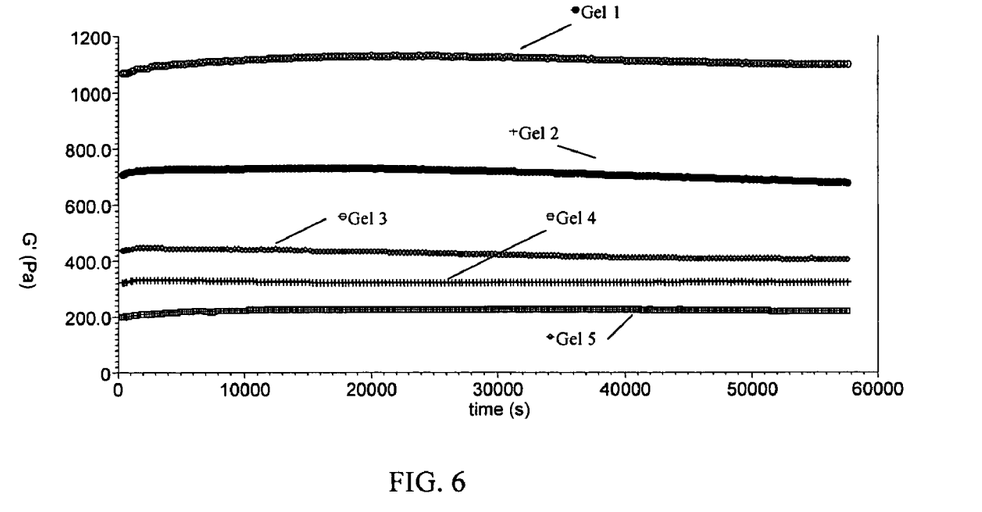
FIG. 6: Degradation profile of the gel of different initial G', prepared from the crosslinked HA of the invention.

FIG. 6 shows ΔG'/Δt over a 16 h period for a range of crosslinked HA compositions having initial storage modulus values between about 200 to about 1200 Pa. The compositions are prepared and the measurements conducted according to the preceding Examples. As can be seen, the degradation of the crosslinked HA compositions is essentially independent of initial storage modulus G' over this 16 hour period.

Example 21

Synergistic Effect of Lidocaine on Rheological Properties of the Gel

Figure 7:
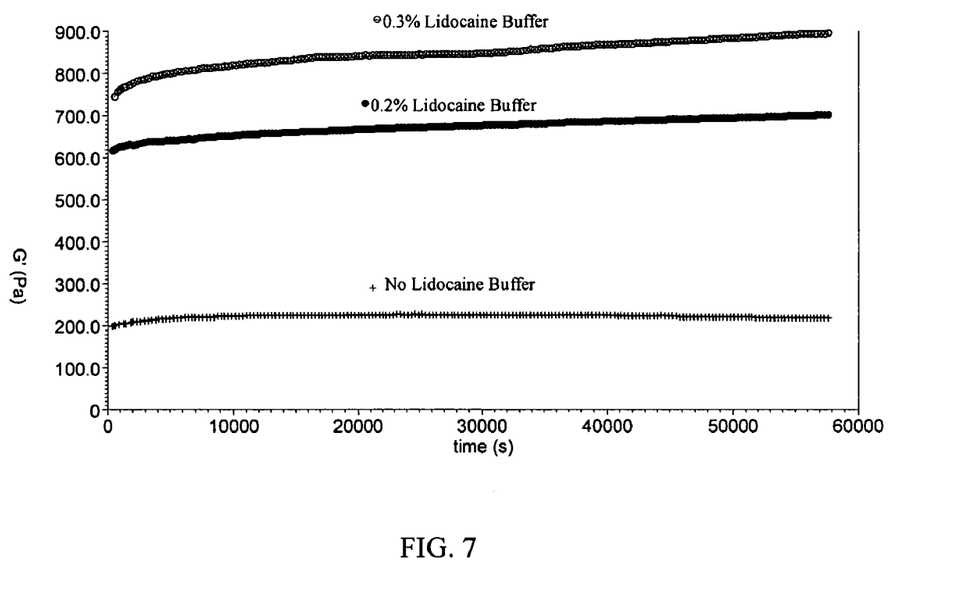
FIG. 7: Storage Modulus G' and degradation profile of the gels prepared in phosphate buffer containing no lidocaine, 0.2% lidocaine, and 0.3% lidocaine.

Lidocaine can have a synergistic effect and increase the initial storage modulus G' of the gel compared to otherwise identical compositions prepared in a buffer without lidocaine. Crosslinked HA of Example-5 was processed as in Example-12 using three separate phosphate buffers 1 (no lidocaine), 2 (0.2% lidocaine), and 3(0.3% lidocaine). Gels were made to 32-mg/mL concentrations and the storage modulus G' and degradation profile ΔG'/Δt of each was measured according to the method described in Example-12. FIG. 7 shows that the compositions with lidocaine have a significantly higher modulus G' over the time of the test. Thus, crosslinked HA with lidocaine can have good biostability, and can in some cases have a synergistic effect, increasing G'.

Example 22

Invention is Effective for Tissue Augmentation

The crosslinked HA product used in the study was prepared according to the procedure described in Example 14. In an Interdermal Injection Study in the Guinea Pig Model, the crosslinked HA product and a control article, (ZYDERM™ II, Collagen, Palo Alto, Calif.), were injected intradermally. Each injection site (6 per time interval per sample) was measured for height and diameter at 2, 4-, 8 and 12-weeks. Specimens were explanted for histological evaluation at each time interval.

Twelve guinea pigs were included in this study and assigned to a termination interval of two animals each at 2, 4, 8, 12, 18, and 24 weeks.

The right and left flank of each animal was clipped free of fur at least 1 hour before dosing. Each animal received six intradermal injections, three per side. The test article and control article were randomized over each animal. Both articles were dosed at 0.2 cc per site. Each site was marked with a non-toxic marker and injection sites were approximately 2 cm apart. In addition, each site was measured for height and diameter at each interval. The measurements immediately after injection were assigned a score of "0". An increase in height and diameter indicated edema.

At each termination interval, three animals were euthanized, the fur clipped, injection site measured, and the site removed and fixed in 10% neutral buffered formalin. The excised tissues were embedded, cut and stained with hematoxylin and eosin (H & E), and examined by a qualified pathologist. Specimens were examined for the presence of the injected article and for any tissue response.

During the first week of the study, erythema scores were minimal (slight) and equally distributed between the test article and Zyderm II injection sites. Edema scores were inconsistent and equally distributed between the two materials. During week two, erythema scores were similar to week one. Edema scores were reduced with most dropping to zero. Injection site measurements at 4-weeks were equivalent to measurements taken immediately after injection.

The volume of CTA was unchanged from 2 weeks to 4 weeks. At 8-weeks observation time, nearly all test article sites continued to maintain height and diameter measurements. Conversely, nearly all control sites were unmeasurable. At 12-weeks observation time, test article was flattened and extended laterally in all sites. However, in the more tissue dense areas of the dermis, the test article did not spread out to the degree as in the less dense areas. Fibroblasts and adipose tissue were located through out the test article at approximately the same density as the tissues adjacent to the injection site. The control article was not identified in any of the injection sites.

Microscopic examination showed no cellular response to test article and only a minor macrophage infiltrate in the control article at 2-weeks and 4-weeks. At 8-weeks and 12-weeks, there was no observable cellular response to either material.

The test articles at 2, 4, 8 and 12-weeks were devoid of any microscopic tissue response, confirming the biocompatibility of this preparation. Upon injection, the test article appeared to integrate into the stromal elements of the dermis. Measurements of height and diameter were unchanged between 2 and 4 weeks. At 8-weeks CTA seemed to extend laterally in the dermal layers, but still maintained its volume. Conversely, the control article appeared as a homogeneous bolus of material compressing the underlying dermis. A minor macrophage infiltrate was observed in the control article at 4-weeks, and at 8-weeks most of the injection had resorbed from the injection site.

The in vivo stability of the test article at 8, and 12-weeks, compared to the control article indicates that this product can exhibit long-term persistence in clinical applications. These results support in vitro data above showing in vivo resistance to degradation by hyaluronidase.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of augmenting tissue in a subject that is in need of tissue augmentation, the method comprising:
   a) inserting a needle into a subject at a location in the subject that is in need of tissue augmentation, wherein the needle is coupled to a syringe loaded with a crosslinked hyaluronic acid (HA) composition that includes crosslinked, water-insoluble, hydrated HA gel particles, wherein the HA includes crosslinks with represented by the following structural formula:

HA'—U—R$_2$—U—HA' wherein:
   each HA' is the same or different crosslinked HA molecule;
   each U is independently an O-acyl isourea or N-acyl urea; and R$_2$ is alkyl, alkenyl, alkynyl, alkoxy, cycloalkyl, cycloalkenyl, cycloalkynyl aryl, heteroaryl, heterocyclyl, cycloaliphaticalkyl, aralkyl, heteroaralkyl, or heterocyclylalkyl,
   wherein the HA gel particles have an average particle diameter distribution selected from the group consisting of a hydrated particle average diameter between about 20 µm and about 1000 µm, and a dehydrated particle average diameter between about 10 µm and about 500 µm;
   wherein the crosslinked HA composition is a single hydrated particle phase; and
   b) applying force to the syringe, whereby at least a portion of the crosslinked HA composition is delivered into the subject;
   wherein the crosslinked HA composition is stable in the subject for at least 8 weeks.

2. The method of claim 1, wherein the subject is human.

3. The method of claim 2, wherein the particles include at least one bioactive agent selected from the group consisting of cells, genes, proteins, antibodies, peptides, and pharmaceuticals.

4. The method of claim 3, wherein the bioactive agent includes an anesthetic.

5. The method of claim 4, wherein the anesthetic is lidocaine, mepivacaine, prilocaine, bupivacaine, cocaine, procaine, chlorocaine, or tetracaine, or a salt or solvate thereof.

6. The method of claim 5, wherein the anesthetic is lidocaine.HCl.

7. The method of claim 2, wherein the distribution is a multimodal distribution.

8. The method of claim 7, wherein the HA in the composition consists essentially of the crosslinked, water-insoluble, hydrated HA gel particles.

9. The method of claim 2 wherein the crosslinked HA composition has at least one parameter measured at 37° C. selected from a storage modulus G' of at least about 50 Pa when measured at 1 Hz frequency using a 4 cm flat geometry, and a kinematic viscosity of at least about 20,000 cPs when measured at a shear rate of 1 s$^{-1}$.

10. The method of claim 9, wherein the composition has a storage modulus G' of at least about 100 Pa.

11. The method of claim 10, wherein the composition has a storage modulus G' of at least about 400 Pa.

* * * * *

UNITED STATES PATENT AND TRADEMARK OFFICE
CERTIFICATE OF CORRECTION

PATENT NO. : 8,124,120 B2
APPLICATION NO. : 10/743557
DATED : February 28, 2012
INVENTOR(S) : Khalid K. Sadozai et al.

Page 1 of 1

It is certified that error appears in the above-identified patent and that said Letters Patent is hereby corrected as shown below:

At column 19, claim 1, line 42, please insert a --,-- directly after "cycloalkynyl".

Signed and Sealed this
Eighteenth Day of December, 2012

David J. Kappos
*Director of the United States Patent and Trademark Office*